United States Patent [19]

Rockett et al.

[11] 4,115,487
[45] Sep. 19, 1978

[54] METHOD FOR DENTAL RESTORATION

[75] Inventors: Thomas J. Rockett, East Greenwich, R.I.; John J. O'Connell, Tustin, Calif.

[73] Assignee: American Hospital Supply Corporation, Evanston, Ill.

[21] Appl. No.: 489,093

[22] Filed: Jul. 17, 1974

Related U.S. Application Data

[62] Division of Ser. No. 416,807, Nov. 19, 1973, abandoned.

[51] Int. Cl.² ............................................. A61C 13/04
[52] U.S. Cl. ........................................ 264/16; 264/19
[58] Field of Search ...................... 106/35; 264/16, 17, 264/18, 19, 20

[56] References Cited

U.S. PATENT DOCUMENTS

| | | | |
|---|---|---|---|
| 2,318,845 | 5/1943 | Feagin | 264/16 |
| 2,514,076 | 7/1950 | Kelly | 264/17 |
| 2,558,139 | 6/1951 | Knock | 264/16 |
| 3,126,429 | 3/1964 | Saffir | 264/20 |
| 3,539,526 | 11/1970 | Bowen | 106/35 |
| 3,801,344 | 4/1974 | Dietz | 106/35 |
| 3,826,778 | 7/1974 | Dietz | 106/35 |

*Primary Examiner*—Robert F. White
*Assistant Examiner*—John A. Parrish
*Attorney, Agent, or Firm*—Tilton, Fallon, Lungmus & Chestnut

[57] ABSTRACT

A method for forming a layered dental restoration in which there is a continuous polymeric resin phase but in which the reinforcing filler compositions of the respective layers are different. A sub-layer, composed of a polymeric resin binder having a refractive index within the range of about 1.53 to 1.56, in admixture with suitable catalysts and a finely-divided reinforcing inorganic filler having a refractive index substantially different than that of such resin, is first applied to the site of restoration and, before the sub-layer has fully cured, a surface layer composed of the same resin and catalysts but a different inorganic filler is applied to the site over the sub-layer. The filler of the surface layer consists essentially of a finely-divided inorganic material having substantially the same refractive index as that of the resin common to both layers.

10 Claims, No Drawings

METHOD FOR DENTAL RESTORATION

RELATED APPLICATION

This is a division of copending application Ser. No. 416,807, filed Nov. 19, 1973, now abandoned.

BACKGROUND

Reinforced polymer matrix composites have gained considerable attention and acceptance in recent years as superior materials for use in restorative dentistry. (See "Guide to Dental Materials and Devices", 4th Ed., Amer. Dent. Assoc., Chicago (1968)). Such composites generally involve a methacrylate-based system in which particles of an inorganic filler are covalently bonded to a resin matrix, or to a coupling agent which is covalently bonded to both. With fillers used to the 80 percent level, polymerization shrinkage and thermal expansion are greatly reduced in comparison with direct filling resins. In terms of stability, solubility, strength and general performance, the ceramic reinforced polymer matrix composites overcome many of the objections raised with regard to earlier silicate cements and direct filling resins.

Ideally, such a restorative material must not only meet or exceed the performance requirements but also be visually indistinguishable from the adjacent natural tooth surfaces. In an effort to achieve invisible or undetectable restorations, prior workers have disclosed that the index of refraction of the ceramic filler should match that of the resin binder, thereby reducing light scattering at the interface between the polymeric binder and each ceramic particle and producing a restoration which is relatively translucent (see U.S. Pat. Nos. 3,539,526 and 3,539,533). Presumably, by making the restorative material as transparent as possible, it has been thought that such material would not obscure the natural tooth color and would not be visually detectable or aesthetically objectionable. Promotional literature for the commercial composites has even emphasized the desirability and importance of such translucence. Unfortunately, despite the translucency or transparency achieved by matching the refractive indices of the binder and filler components, restorations made with such composites are often noticeable and therefore aesthetically unsatisfactory.

As disclosed in co-pending co-owned Rockett et al application Ser. No. 507,223, filed Sept. 18, 1974, now U.S. Pat. No. 4,020,557, which was a CIP of application Ser. No. 416,808, filed Nov. 19, 1973, now abandoned, it has recently been discovered that in specific applications aesthetically superior restorations may be made with a composite in which there is a substantial mismatch between the refractive indices of the filler and binder, especially where such mismatch is accompanied by a match between the refractive indices of the filler and the hydroxy apatite of teeth. Since such a composite is relatively opaque, the precise reasons for its aesthetic effectiveness as a restorative material are still not definitely and completely known, particularly in view of the aforementioned teachings of the prior art concerning the importance of achieving a high degree of translucency. As noted in that application, however, the relatively opaque composite material, although aesthetically superior in some applications to the earlier and more translucent composites, still produces visually detectable restorations in a number of instances, for example, in those cases where restorations occur along the marginal edges of teeth.

Other patents and literature showing the state of the prior art are U.S. Pat. Nos. 3,066,112, 3,200,142, and 3,635,889, and the references cited therein; Bowen R. L. et al, "Composite Restorative Materials," paper given at 50th Anniversary Symposium on Dental Material Research, NBS, Oct. 6–8, 1969; L. J. Brontman et al, "Modern Composite Materials", Addison-Wesley Publishing Co., Reading, Mass. (1967); R. L. Bowen, "Effect of Particle Shape and Size Distribution in a Reinforced Polymer," J. ADA, Vol. 64, p. 481 (1964); W. Souder et al, "Physical Properties of Dental Materials," National Bureau of Standards Circular C433, U.S. Government Printing Office, Washington, D.C. (1942).

SUMMARY

The present invention involves the discovery that a substantial further improvement in the aesthetics of dental restorations is achieved, without impairing or reducing the strength, durability, and other important physical characteristics which filled polymer matrix composites are known to possess, by forming a double-layered restoration having a continuous resin phase. The base layer, or sublayer, comprises a conventional polymeric resin binder having a refractive index within the range of about 1.53 to 1.56 and a reinforcing filler of finely-divided inorganic particles which are bonded to the resin matrix and which have a refractive index substantially different than that of the resin. Specifically, the refractive index of the filler material should fall within the range of about 1.58 to 1.66 with an optimum value of approximately 1.63. After the sub-layer has been applied at the site of dental restoration, and before the resin has fully cured, a surface layer is applied. The surface layer is composed of the same resin used in the sub-layer but, unlike the sub-layer, the surface layer contains as a major constituent a reinforcing filler consisting essentially of an inorganic material having a refractive index which matches or closely approximates the refractive index of the resin. The result is a unitary dental restoration which has a continuous resin phase but which nevertheless is composed of successive layers differing in opacity or translucency.

A further aspect of the invention lies in the method of using a three-part composite system for making the two-layered dental restorations. Part one of that system is a mixture comprising a minor proportion of the polymeric resin binder having a refractive index when cured within the range of 1.53 to 1.56 and a major proportion of the finely-divided reinforcing filler which is capable of being coupled to that binder and which has a refractive index matching or approximating that of the binder. Part two includes a mixture of the same resin binder used in part one along with a major proportion of a different reinforcing filler having a refractive index substantially different from the refractive index of the resin. In addition, parts one and two may each contain measured quantities of the same component of a co-catalyst system. Part three includes the catalyst and, if a co-catalyst system is employed, would contain the second component of the co-catalyst system in sufficient quantity so that divided portions of part three could be mixed with parts one and two to cause complete curing of the resin of parts one and two. Part three may be in the form of a liquid or, if desired, may also include predetermined quantities of the same resin and filler used in part one and, as a result, may take the form of a paste. In use, a dentist or dental technician simply mixes measured quantities of parts two and three to form the composite for the sub-layer, and mixes measured quantities of parts one and three to form the composite for the surface layer.

DETAILED DESCRIPTION

As already indicated, this invention is believed useful in conjunction with any of the standard polymeric resin binders useful for preparing dental composites, such binders generally being methacrylate based and, when cured, having refractive indices within the general range of 1.53 to 1.56. For that reason, and because information concerning the formulation and preparation of such binders, and the coupling agents used therewith, is well known and readily available, as indicated by the citations already given, a detailed discussion of such resin binders is believed unnecessary herein. A typical formulation would contain a crosslinking dimethacrylate monomer (such as the monomeric reaction product of 4,4'-isopropylidenediphenol and glycidyl methacrylate commonly called BIS-GMA), along with a comonomer for reducing the viscosity of the liquid phase (such as methylmethacrylate or ethyleneglycol dimethacrylate), color stabilizers, and polymerization inhibitors. Such an inhibitor acts as a free radical trap to inhibit the premature polymerization of the methacrylate monomers, and may take the form of hydroquinone, substituted hydroquinones, or a hindered phenol such as 2,6,-di-tert-butyl-p-cresol.

Any suitable catalyst may be used to produce polymerization of the monomers, such catalysts being well known and described fully in the prior art. A co-catalyst system, such as an organic peroxide used in conjunction with an aromatic tertiary amine, has been found particularly effective although single catalyst systems might also be used. In a co-catalyst system, the amine is commonly referred to as an accelerator but, since such accelerator functions generally as a co-catalyst, both terms are believed appropriate herein. A typical co-catalyst system might consist of benzoyl peroxide as one component and N,N'-dimethyl-3,5-dimethyl aniline as the other.

A silane coupling agent, such as trialkoxysilane containing an organic function, may be used to promote adhesion between the binder and filler material in a manner as fully disclosed in prior art. It is to be understood, however, that the use of a silane coupling agent may not be necessary or even desirable in all cases and that techniques are available, or may become available, for the direct bonding of the filler to the polymeric matrix.

As previously stated, the product takes the form of three separate components which are mixed in a specified manner by the dentist or technician at the time a dental restoration is to be made. Part one consists essentially of the resin described above in admixture with a finely-divided non-toxic inorganic filler having a refractive index which matches or closely approximates that of the resin. Crystalline silica (quartz) particles (refractive index of 1.56), fused (vitreous) silica (refractive index of 1.54), or any other suitable material having a similar index of refraction may be used. Particularly effective results have been obtained using relatively soft (approximately 5.3 Moh) silicate glass of the type disclosed in the aforementioned co-pending application (refractive index 1.55). For purposes of this invention, any non-toxic inorganic compound, either crystalline or amorphous, which is capable of being finely divided, takes the form of a whitish powder, is substantially insoluble in water, and has a refractive index closely matching that of the resin may be used. The size of such particles should be no greater than 50 microns, preferably falling within the range of 2 to 25 microns.

The filler material may be reduced to microparticle size by ball milling or by any other suitable grinding or milling procedure. All impurities or contaminants should be avoided or removed from the powder. Thereafter, the particles may optionally be coated with a suitable coupling agent as indicated above and as fully disclosed in the prior art of record. The particles are then blended with the resin (in the proportion of approximately 65 to 80 percent by weight of filler) to form the polymerizable premixture referred to herein as "part one" of the dental composite. Where a co-catalyst system is used, one of the components of that system (the accelerator) would also be premixed with the resin and filler of part one.

Part two is identical to part one except that a different filler is used. Unlike the inorganic filler of part one, the filler used in part two consists essentially of a finely-divided inorganic compound having a refractive index substantially different than that of the resin. More specifically, the filler of part two should have a refractive index within the range of 1.58 to 1.66, the optimum refractive index being about 1.63, the index of refraction of hydroxy apatite. Some of the materials suitable for this purpose are anisotropic and have plural indices of refraction; in those cases, it is to be understood that the term "index of refraction" (or "refractive index") as used herein means the average index of refraction. Minerals and other inorganic compounds, all of which have indices of refraction between 1.58 and 1.66 and which are believed suitable for use as fillers for purposes of this invention, include the following:

| | |
|---|---|
| Wollastonite | $CaO \cdot SiO_2$ |
| Tremolite | $CaMg_3(SiO_4)_3$ |
| Whitlockite | $Ca_3(PO_4)_2$ |
| Fluroapatite | $CaF_2 \cdot 3Ca_3P_2O_8$ |
| Magnesium pyrophosphate | $Mg_2P_2O_7$ |
| para Hopeite | $Zn_3(PO_4)_2 \cdot 4H_2O$ |
| Lithium aluminate | $LiAlO_2$ |
| Silimanite, Andalusite | $Al_2O_3 \cdot SiO_2$ |
| Mullite | $3Al_2O_3 \cdot 2SiO_2$ |
| Prehnite | $2CaO \cdot Al_2O_3 \cdot 3SiO_2 \cdot H_2O$ |
| Topaz | $2AlFO \cdot SiO_2$ |
| Alumina | $Al_2O_3 \cdot H_2O$ |
| Chondroite | $[Mg(F,OH)_2Mg_3[SiO_4]_2$ |
| Hemimorphite | $2ZnO \cdot SiO_2 \cdot H_2O$ |

Wollastonite has been found particularly effective as the filler material because its average refractive index is 1.63 and because it may be securely bonded to the resin matrix with the use of silane coupling agent. However, wollastonite in its natural form has physical characteristics which tend to limit the proportional amount of such filler that may be mixed with the resin. It has been found that the fibrous crystals of natural wollastonite (form A) tend to stack upon each other in a manner that limits the amount of filler to under 70 percent. Grinding, in order to reduce particle size and increase packing, does not effectively solve the problem because the crystals shear longitudinally, retaining their fibrous form. To overcome such problems, pseudowollastonite (form B) may be prepared by reacting sodium metasilicate with calcium chloride to produce an amorphous precipitate of calcium silicate. After thorough washing, the precipitate is fired to approximately 1450° C., just below the melting point of wollastonite but above the temperature (1150° C.) at which a transition occurs from form A to form B. The wollastonite (or pseudowollastonite) is then quenched and the material in its B phase is milled until the particles are of a size within the range already specified. The result is a synthesized wollastonite in the form of a fine powder which is similar to natural wollastonite except that the particles are not fibrous and have substantially higher compressive strength. Because of the non-fibrous nature of the particles, filler loadings of 70 to 80 percent are possible.

Part three of the composite preparation essentially comprises the catalyst for triggering polymerization of the resin components of parts one and two. Thus, in the co-catalyst system previously described, the essential ingredient, and if desired the only ingredient, of part three would be benzoyl peroxide. The solution of benzoyl peroxide may be supplied in a single container, from which measured portions would be extracted or removed for mixing with parts one and two when a dental restoration is to be made, or such portions may be packaged in separate containers. To facilitate mixing and blending of the ingredients by the dentist or technician, the catalyst may be premixed, to form a paste, with a resin of the same composition used in the other parts and with a filler of the same composition used in part one. Consequently, when measured quantities of parts one and three are mixed just prior to application, the filler as so combined will still have essentially the same refractive index as the resin which is common to both parts. On the other hand, when parts two and three are mixed together just prior to application, a relatively opaque mixture will still be formed because of the inclusion in the premix of part two of a filler having a refractive index within the range of 1.58 to 1.66.

In using the three-part composite preparation, a dentist first intimately mixes a portion of part three with an equivalent portion of part two and applies the mixture to the prepared site for dental restoration. The mixture may be worked and smoothed in place using suitable dental instruments and, after initial hardening or setting (usually within 4 minutes) may be sculptured or ground as desired. Before curing of the sub-layer has completely occurred, that is, within a period of approximately 4 to 6 minutes, the materials for the surface layer (parts one and three) are mixed and applied. The surface layer is applied to cover the sub-layer and is worked and smoothed in place with suitable tools. After setting, the outer or surface layer is then finished and polished using conventional dental tools and techniques.

The invention may be more fully understood from the following illustrative examples:

The surface layer is applied to cover the sub-layer and is worked and smoothed in place with suitable tools. After setting, the outer or surface layer is then finished and polished using conventional dental tools and techniques.

The invention may be more fully understood from the following illustrative examples:

EXAMPLE 1

A dental product in which the product takes the form of three separate components, which are mixed in a specified manner by the dentists or technician at the time a dental restoration is to be made.

The filler material for part one may be prepared as follows. Dissolve 212.15 grams sodium silicate pentahydrate in 3,000 milliliters distilled water and mix with a solution of 111 grams of calcium chloride dissolved in 750 milliliters of distilled water to form an amorphous precipitate of calcium silicate. After being washed and dried the precipitate is placed in a platinum lined crucible, heated to a temperature of 1400°–1425° C. for 45 minutes, quenched in cold water and then thoroughly dried. The pseudowollastonite thus prepared is then ground in a ball mill until the average particle size is below 20 microns.

The filler for part two is composed of a silicate glass consisting of 51.43% $SiO_2$, 22.67% $Al_2O_3$, and 23.33% MgO, as available from Pemco Division of SCM Corporation, Baltimore, Maryland. This glass is characterized by being relatively soft, having a hardness on the Moh scale between 5 and 5.5 and having a refractive index of 1.55.

A silane solution for treating both of the above fillers is prepared by mixing 4 grams of α-methacryloxypropyltrimethoxysilane with 130 grams of methanol and 20 grams of distilled water. This solution is then equally divided and to each portion is added and mixed 400 grams of the respective fillers. The mixtures are then placed in an oven, heated to 65° C. to evaporate excess liquid and thereafter heated at 110° C. for two hours. After washing with acetone, the treated fillers are then dried in an oven at 110° C.

The resin to be used as a binder for both these fillers may be prepared by mixing 1.5 grams of Permasob MA, 70 grams of bis BMA, 15 grams of trimethylolpropane-trimeth-acrylate, 15 grams of ethyleneglycoldimethacrylate and 0.05 grams of 2,5-di-t-butyl-p-cresol. These maters should be heated gently until a homogenous mixture is formed.

Part one of the system is prepared by first mixing 0.675 grams of n-tolyldiethanolamine and 45 grams of the base resin until a homogenous mixture is formed. 180 grams of the treated alumino silicate glass powder is then slowly added and mixing continued until a homogenous paste is formed.

Part two of the system is prepared by first mixing 0.675 grams of n-tolyldiethanolamine and 45 grams of the base resin, until a homogenous mixture is formed. To this mixture is then added 180 grams of the treated wollastonite filler powder and mixing is continued until a homogenous paste is formed.

Part three of the system is prepared by first mixing 1.8 grams of benzoyl peroxide (catalyst paste) and 45 grams of the base resin. Then after a homogenous mixture is formed, slowly adding 180 grams of the treated aluminosilicate powder. Again, the mixing is continued until a homogenous paste is formed.

EXAMPLE 2

A composite prepared in accordance with the above example was used to make a series of dental restorations on human patients. Standard FG latch and straight handpiece burs were used in the preparation of the cavity. Standard cavity preparations similar to those used for amalgams, silicate and other plastics are acceptable for this three-part system. The final step of preparing the composites was undertaken by first mixing equal quantities of parts two and three. These two materials gave a self-curing optically opaque material which was used to repair dentin areas. After that sub-layer was applied, a second mixture of equal parts of part one and part three was prepared and placed over the sub-layer to give it an enamel-like finish. After setting, the surface layer was then finished and polished using conventional dental tools and techniques. Visible observations of the final restorations made by the above procedure have shown excellent aesthetic qualities, better than those normally attained by conventional procedures and materials.

EXAMPLE 3

A dental composite was prepared in accordance with the procedures of Examples 1 and 2, except that part three consisted only of a liquid solution of 100 parts of dimethylphthalate and 15 parts of benzoyl peroxide. This catalyst solution was then used to catalyze the polymerization of both parts one and two. In using such liquid catalyst, the ratio of paste-to-liquid was approximately a 2 milligram drop of the dimethylphthalate liquid to 0.25 grams of either parts one and two. An advantage of using a liquid catalyst was found to reside in the fact that all parts of the system were relatively insensitive to temperature changes and exhibited relatively long shelf life even at highly elevated storage temperatures.

While in the foregoing we have disclosed embodiments of the invention in considerable detail for purposes of illustration, it will be understood that many of those details may be varied without departing from the spirit and scope of the invention.

We claim:

1. A method for forming dental restorations comprising the steps of mixing and applying to a site requiring dental restoration a composite sub-layer comprising a mixture of a polymerizable resin binder having a refractive index within the range of about 1.53 to 1.56, a reinforcing filler comprising a finely-divided inorganic compound having a particle size no greater than about 50 microns and having a refractive index substantially different than the refractive index of said resin, and a catalyst for curing said resin; and mixing and applying to the same site, over said sub-layer and before the resin of said sub-layer has fully cured, a composite surface layer comprising the same resin and catalyst components used in said sub-layer in admixture with a reinforcing filler consisting of a finely-divided inorganic compound having a particle size no greater than about 50 microns and having substantially the same refractive index as that of said resin, whereby, a double-layered dental restoration is formed having different refraction characteristics in each layer and having a continuous resin phase.

2. The method of claim 1 in which the reinforcing filler of said sub-layer consists of an inorganic compound having a refractive index above that of said resin.

3. The method of claim 2 in which the inorganic filler of said sub-layer has a refractive index within the range of 1.58 to 1.66.

4. The method of claim 3 in which said inorganic filler of said sub-layer has a refractive index of approximately 1.63.

5. The method of claim 3 wherein the inorganic filler of said sub-layer is selected from the grouping consisting of wollastonite, tremolite, whitlockite, fluroapatite, magnesium pyrophosphate, para hopeite, alumina, lithium aluminate, silimanite, andalusite, mullite, prehnite, topaz, chondroite, and hemimorphite.

6. The method of claim 5 in which said inorganic filler of said sub-layer is crystalline wollastonite, the crystals of wollastonite being in their high temperature B form.

7. A method of forming dental restorations with a three-part composite system in which part one of said system comprises a premix of a polymerizable resin binder having a refractive index when cured within the range of 1.53 to 1.56 and a finely-divided reinforcing filler capable of being coupled to said resin binder, said filler having a particle size no greater than about 50 microns and having a refractive index substantially the same as said binder, part two comprises a premix of a resin binder of the same composition as the binder of part one and a finely-divided reinforcing filler having a particle size no greater than about 50 microns and having a refractive index substantially above the refractive index of said resin binder, and part three comprises at least one catalyst for polymerizing the resin binder common to parts one and two, comprising the steps of
intimately mixing a portion of part three with a selected quantity of part two and thereafter applying such mixture to a dental site requiring dental restoration to form a curable composite sub-layer at said site, and intimately mixing another portion of part three with a selected quantity of part one and thereafter applying such mixture to the same site, before the resin of the sub-layer has fully cured, to form a composite surface layer over said composite sub-layer, whereby a double-layered dental restoration is formed having different refraction properties in each layer and having a continuous resin phase.

8. The method of claim 7 in which the filler of part two has a refractive index within the range of 1.58 to 1.66.

9. The method of claim 8 in which the filler of part two has a refractive index of approximately 1.63.

10. The method of claim 7 in which the filler of part two is selected from the grouping consisting of wollastonite, tremolite, whitlockite, fluroapatite, magnesium pyrophosphate, para hopeite, alumina, lithium aluminate, silimanite, andalusite, mullite, prehnite, topaz, chondroite, and hemimorphite.

* * * * *